(12) United States Patent
Anderskewitz et al.

(10) Patent No.: US 6,528,491 B2
(45) Date of Patent: Mar. 4, 2003

(54) PYRANOSIDE DERIVATIVES

(75) Inventors: Ralf Anderskewitz, Bingen (DE); Kurt Schromm, Ingelheim (DE); Franz Birke, Ingelheim (DE); Hans Michael Jennewein, Wiesbaden (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/047,526

(22) Filed: Oct. 23, 2001

(65) Prior Publication Data

US 2002/0128209 A1 Sep. 12, 2002

Related U.S. Application Data

(60) Provisional application No. 60/250,661, filed on Dec. 1, 2000.

(30) Foreign Application Priority Data

Oct. 24, 2000 (DE) .......................... 100 52 658

(51) Int. Cl.$^7$ ................ A01N 43/04; A61K 31/70; C07G 11/00; C07H 15/00; C07C 211/00
(52) U.S. Cl. .................. 514/25; 514/27; 514/637; 536/4.1; 536/16.8; 564/247; 564/244; 564/384; 564/385; 564/389
(58) Field of Search ............ 514/25, 27, 637; 564/247, 244, 384, 385, 389; 536/4.1, 16.8

(56) References Cited

U.S. PATENT DOCUMENTS

| | | | |
|---|---|---|---|
| 5,686,496 A | * | 11/1997 | Anderskewitz et al. |
| 5,731,332 A | * | 3/1998 | Anderskewitz et al. |
| 6,037,377 A | * | 3/2000 | Anderskewitz et al. |
| 6,127,423 A | | 10/2000 | Anderskewitz et al. |
| 6,197,753 B1 | | 3/2001 | Anderskewitz et al. |
| 6,197,824 B1 | | 3/2001 | Schromm et al. |
| 6,265,612 B1 | | 7/2001 | Schromm et al. |
| 6,288,277 B1 | * | 9/2001 | Anderskewitz et al. |
| 6,291,531 B1 | * | 9/2001 | Anderskewitz et al. |
| 6,489,365 B1 | * | 12/2002 | Anderskewitz et al. |

FOREIGN PATENT DOCUMENTS

| | | |
|---|---|---|
| WO | WO 98 11062 A | 3/1998 |
| WO | WO 98 11119 A | 3/1998 |

* cited by examiner

*Primary Examiner*—James O. Wilson
*Assistant Examiner*—Traviss C. McIntosh
(74) *Attorney, Agent, or Firm*—Robert P. Raymond; Philip I. Datlow; Alan R. Stempel

(57) ABSTRACT

The present invention relates to new pyranoside derivatives of general formula I, processes for preparing them as well as their use as medicaments:

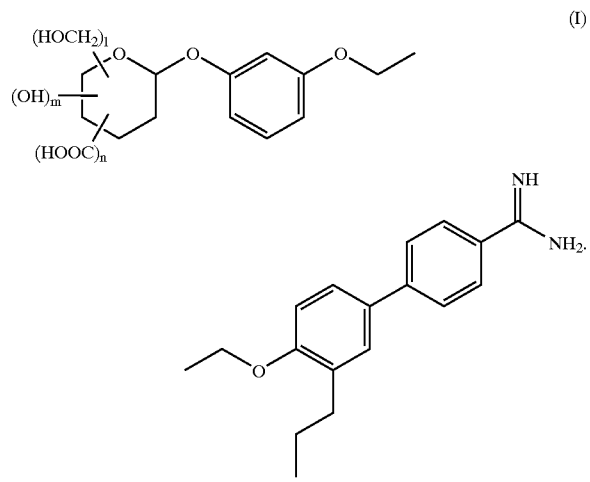

11 Claims, No Drawings

PYRANOSIDE DERIVATIVES

RELATED APPLICATIONS

Benefit of U.S. Provisional Application Serial No. 60/250,661, filed on Dec. 1, 2000 is hereby claimed, and said Application is herein incorporated by reference.

DETAILED DESCRIPTION OF THE INVENTION

The present invention relates to new pyranoside derivatives, processes for preparing them as well as their use as medicaments. The new pyranoside derivatives correspond to general formula I

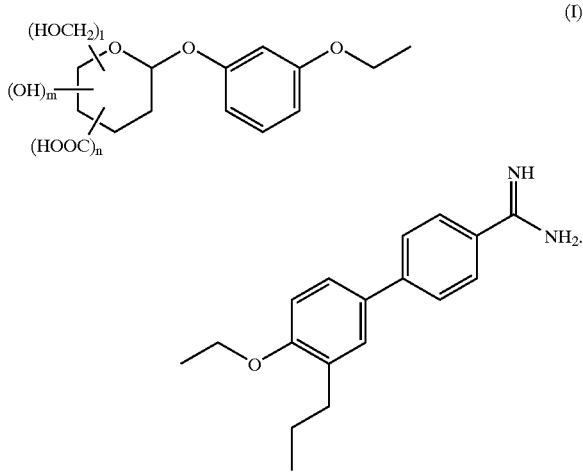

wherein
l, m and n denote an integer 0, 1, 2, 3 or 4 and $l+m+n \leq 4$
in the form of their racemates, in enantiomerically pure or enriched form, optionally as pairs of diastereomers and as the free bases or salts, preferably with physiologically acceptable acids.
Preferred compounds of formula I are those wherein
m is 3,
l and n each denote 0 or 1, and
l+n is 1.
Particularly preferred compounds correspond to formula IA,

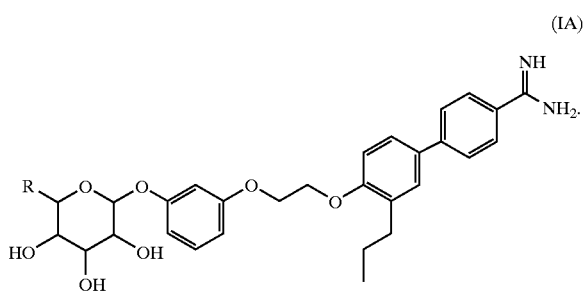

wherein R denotes COOH or $CH_2OH$.

In particular, the compounds according to the invention 3'-n-propyl-4'-[2-(3-hydroxyphenoxy)-ethoxy]-1,1'-biphenyl-4-carboximidamide-O-β-D-glucuronide and 3'-n-propyl-4'-[2-(3-hydroxyphenoxy)-ethoxy]-1,1'-biphenyl-4-carboximidamide-O-glucose are potent $LTB_4$-antagonists.

The compound of Example 1 is formed in vivo as a metabolite of an $LTB_4$-antagonistic compound and has a $K_i$-value of 3.6 nM in the receptor binding test.

As has been found, the compounds of formula I are characterised by their versatility of use in the therapeutic field. Particular emphasis should be laid on those applications for which the $LTB_4$-receptor-antagonistic properties play a part. The following should be mentioned in particular: arthritis, asthma, chronic obstructive lung diseases such as chronic bronchitis, psoriasis, ulcerative colitis, gastro- or enteropathy induced by nonsteroidal antiphlogistics, cystic or pulmonary fibrosis, Alzheimer's disease, shock, reperfusion damage/ischaemia such as stroke or cardiac infarct, atherosclerosis, multiple sclerosis, autoimmune diseases, malignant neoplasia, alveolitis.

The new compounds may also be used to treat illnesses or conditions in which the passage of cells from the blood through the vascular endothelium into the tissues is of importance (such as metastasis) or illnesses and conditions in which the combination of $LTB_4$ or another active substance (such as 12-HETE) with the $LTB_4$ receptor has an influence on cell proliferation (e.g. chronic myeloid leukaemia).

The new compound may also be used in conjunction with other active substances, e.g. those which are used for the same indications, or e.g. with antiallergic agents, secretolytics, $β_2$-adrenergics, steroids taken by inhalation, antihistamines, $PDE_4$ inhibitors, peptido-leukotriene antagonists and/or PAF antagonists. They may be administered topically, orally, transdermally, nasally, parenterally or by inhalation.

The activity can be investigated pharmacologically and biochemically using tests as disclosed for example in WO 93/16036, pp. 15 to 17; reference is hereby made to the contents of this publication.

The therapeutic or prophylactic dose depends—apart from the potency of the individual compounds and the patient's body weight—on the nature and gravity of the condition. For oral administration the dosage is between 10 and 500 mg, preferably between 20 and 250 mg. By inhalation the amount of active substance delivered to the patient is between about 0.5 and 25, preferably between about 2 and 20 mg.

Solutions for inhalation generally contain between about 0.5 and 5% of active substance. The new compounds may be administered in conventional preparations, e.g. as plain or coated tablets, capsules, lozenges, powders, granules, solutions, emulsions, syrups, aerosols for inhalation, ointments and suppositories.

The following Examples show some possible ways of formulating the preparations:

EXAMPLES OF FORMULATIONS

1. Tablets
   Composition:

| | |
|---|---|
| Active substance according to the invention | 20 parts by weight |
| Stearic acid | 6 parts by weight |
| Glucose | 474 parts by weight |

The ingredients are processed in the usual way to form tablets weighing 500 mg. If desired, the active substance content may be increased or reduced and the quantity of glucose reduced or increased accordingly.

2. Suppositories
Composition:

| | |
|---|---|
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

3. Powder for Inhalation

Micronised powdered active substance (compound of formula I; particle size about 0.5 to 7 μm) is packed into hard gelatine capsules in quantities of 5 mg, optionally with the addition of micronised lactose. The powder is inhaled from conventional inhalers, e.g. according to DE-A 33 45 722, to which reference is hereby made.

The compounds according to the invention compound are prepared using methods known per se from the prior art. Thus, the compounds of general formula I may be prepared by reacting the 3'-n-propyl-4'-[2-(3-hydroxyphenoxy)-ethoxy]-1,1'-biphenyl-4-carboximidamide of formula II known from WO 98/11062 (corresponding to U.S. Pat. No. 6,197,824 B1), in the form of the corresponding phenoxide

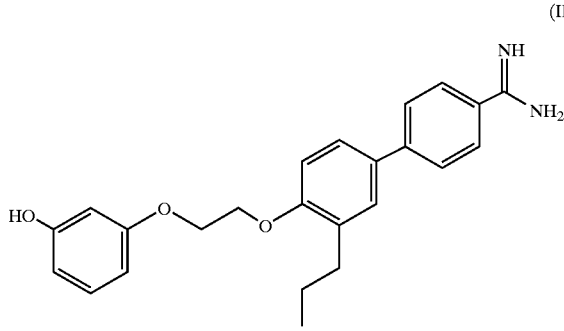

(II)

with a glucose derivative of general formula III,

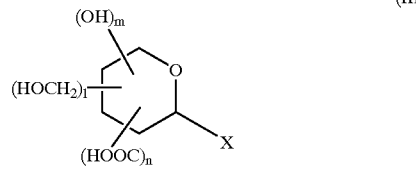

(III)

wherein l, m and n are as hereinbefore defined, and in the event that n>0 the carboxyl group is optionally protected in the form of a $C_1$–$C_4$-alkylester and the hydroxyl groups are protected in the form of acyl groups with an aliphatic or aromatic carboxylic acid, and X denotes a leaving group which may be substituted by a phenoxide oxygen, as the phenoxide and optionally the ester groups are saponified.

The compounds according to the invention may moreover be prepared from an optionally protected glucose derivative (III) and the abovementioned phenol (II) using basic heavy metal compounds such as, for example, $Ag_2O$ or $CdCO_3$ in inert solvents such as toluene or dichloromethane. If desired, the product may be liberated by saponification of the protecting groups.

The compounds (I) may also be prepared from derivatives of formula (III) and the abovementioned phenol (II) using Lewis acids such as, for example, $BF_3$, $AlCl_3$, $ZnCl_2$, $SnCl_4$ or $TiCl_4$ or from alkoxide derivatives of these Lewis acids in inert solvents such as toluene, dichloromethane etc.

Moreover, the compounds according to the invention may be prepared from an optionally protected derivative (III) with X=OH and the abovementioned phenol using acid catalysts such as, for example, methanesulphonic acid or tetrafluoroboric acid or using Lewis acids such as, for example, $BF_3$, $AlCl_3$, $ZnCl_2$, $SnCl_4$ or $TiCl_4$, or from alkoxide derivatives of these Lewis acids in inert solvents such as aliphatic, aromatic, alkyl-substituted aromatics or in a halogenated hydrocarbon—preferably in toluene or in dichloromethane.

$C_1$–$C_4$-alkyl for the purposes of the preparation processes described above generally denotes a branched or unbranched hydrocarbon group with 1 to 4 carbon atom(s), which may optionally be substituted by one or more halogen atom(s), preferably fluorine, which may be identical to or different from one another. The following hydrocarbon groups are mentioned as examples:

methyl, ethyl, propyl, 1-methylethyl (isopropyl), n-butyl, 1-methylpropyl, 2-methylpropyl and 1,1-dimethylethyl.

In a particularly preferred embodiment of the process according to the invention, 4'-[2-(3-hydroxyphenoxy) ethoxy]-3'-propyl-1,1'-biphenyl]-4-carboximidamide or an acid addition salt thereof is reacted with an alkyl acetobromo-α-D-glucuronate in the presence of a base, preferably a metal alkoxide, particularly sodium methoxide, most preferably in the form of a 30% solution in methanol, in an inert solvent, preferably an ether such as for example diethylether or tetrahydrofuran, a polyether such as for example dimethoxyethane, an alcohol such as, for example, methanol or ethanol, or a mixture of these solvents at a temperature from −80 to +100° C., from −40 to +80° C., particularly from −25 to +40° C. Under the preferred conditions described above, the reaction is generally over in 2 to 36 hours, preferably 6 to 18 hours.

The compounds according to the invention may be prepared, starting from compounds known from the prior art, using the processes described in the following Examples, inter alia. Various other embodiments of the process will be apparent to anyone skilled in the art from the present specification. It is specifically pointed out, however, that these Examples and the related description are provided solely as an illustration and are not to be regarded as restricting the invention.

EXAMPLE 1

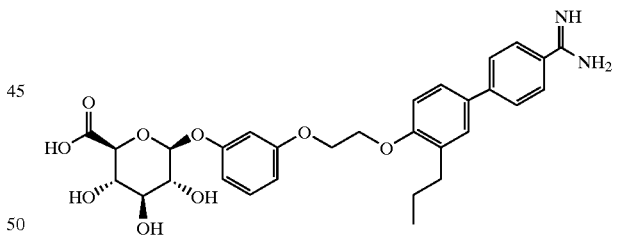

3'-n-propyl-4'-[2-(3-hydroxyphenoxy)-ethoxy]-1,1'-biphenyl-4-carboximidamide-O-β-D-glucuronide 4 g of 4'-[2-(3-hydroxyphenoxy)ethoxy]-3'-propyl-1,1'-biphenyl])-4-carboximidamide monochloride, 3.8 ml of sodium methoxide (as a 30% solution in methanol) in 100 ml of dimethoxyethane are slowly added in two batches at −20–30° C. to 3–5 g of methyl cetobromo-α-D-glucuronate in 50 ml of methanol and stirred for 12 hours. The mixture is combined with ether and the supernatant is poured off. The oil is filtered in ethyl acetate/methanol over a little silica gel and concentrated by evaporation. The residue is stirred in 100 ml of methanol and a solution of 0.5 g of LiOH in 5 ml of water for 90 minutes at ambient temperature and concentrated by evaporation. After purification by chromatography, 1.1 g of the target compound are obtained, m.p. >100° C. (decomposition).

EXAMPLE 2

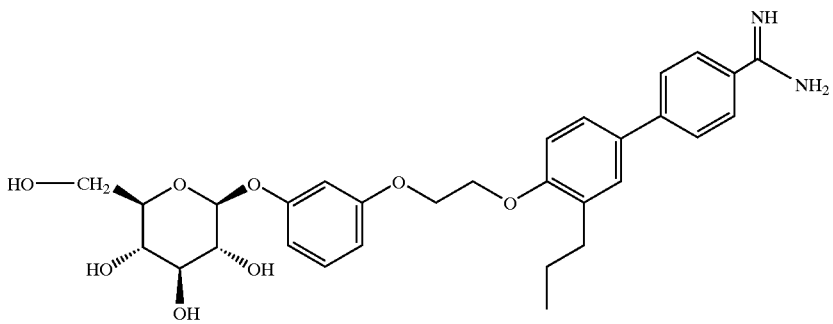

3'-n-propyl-4'-[2-(3-hydroxyphenoxy)-ethoxy]-1,1'-biphenyl-4-carboximidamide-O-glucose The compound is prepared using the method in Example 1 from 3'-n-propyl-4'-[2-(3-hydroxyphenoxy)-ethoxy]-1,1'-biphenyl-4-carboximidamide and tetraacetylbromoglucose.

What is claimed is:

1. A compound of formula I:

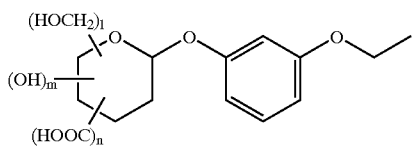

(I)

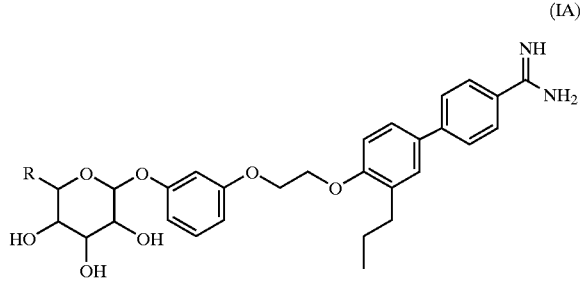

wherein l, m and n denote an integer 0, 1, 2, 3 or 4 and $l+m+n \leq 4$ in the form of its racemate, an enantiomerically pure or enriched form, pairs of diastereomers, the free base or a salt with a physiologically acceptable acid.

2. A compound of formula I according to claim 1, wherein m is 3, l and n each denote 0 or 1, and l+n is 1.

3. A compound of formula IA:

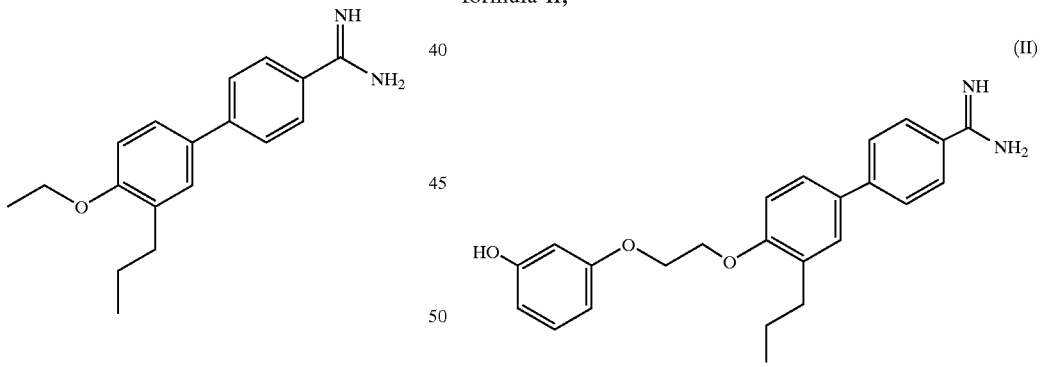

(IA)

wherein R denotes COOH or $CH_2OH$.

4. 3'-n-Propyl-4'-[2-(3-hydroxyphenoxy)-ethoxy]-1,1'-biphenyl-4-carboximidamide-O-β-D-glucuronide.

5. 3'-n-Propyl-4'-[2-(3-hydroxyphenoxy)-ethoxy]-1,1'-biphenyl-4-carboximidamide-O-glucose.

6. A process for preparing a compound of formula I according to claim 1, wherein a hydroxybenzamidine of formula II, (II)

is reacted with a glucose derivative of formula III

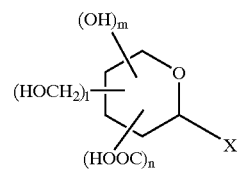

(III)

wherein l, m and n are defined as in claim 1, and in the event that n>0 the carboxyl group is optionally protected in the form of a $C_{1-4}$-alkylester and any hydroxyl groups are protected in the form of acyl groups using an aliphatic or aromatic carboxylic acid, and X denotes a leaving group which may be substituted by a phenoxide oxygen, and the phenoxide and optionally any ester groups are saponified.

7. A process according to claim 6, wherein the reaction is carried out in the presence of an acid catalyst or a Lewis acid.

8. A process according to claim 6, wherein the reaction is carried out in the presence of a basic transition metal compound.

9. A pharmaceutical composition comprising a compound according to claim 1 and a pharmaceutically acceptable carrier and/or excipient.

10. A method of treating a disease that is responsive to $LTB_4$-antagonistic activity comprising administering to a host need thereof a therapeutically effective amount of one or more compounds according to claim 1 or the stereoisomers thereof or the acid addition salts thereof.

11. A method according to claim 10, wherein the disease that is treated is selected from arthritis, asthma, chronic obstructive pulmonary disease, psoriasis, ulcerative colitis, gastro- or enteropathy induced by nonsteroidal antiphlogistics, cystic or pulmonary fibrosis, Alzheimer's disease, shock, reperfusion damage/ischaemia, atherosclerosis, multiple sclerosis, autoimmune diseases, malignant neoplasia, alveolitis.

* * * * *